(12) United States Patent
Xu et al.

(10) Patent No.: US 12,390,411 B2
(45) Date of Patent: **\*Aug. 19, 2025**

(54) PERSONAL CARE COMPOSITION COMPRISING A SILICON GLYCAN

(71) Applicants: Rohm and Haas Company, Collegeville, PA (US); Dow Silicones Corporation, Midland, MI (US); Union Carbide Corporation, Seadrift, TX (US)

(72) Inventors: Wenjun Xu, Phoenixville, PA (US); Marc-Andre Courtemanche, Midland, MI (US); Emmett M. Partain, III, Bound Brook, NJ (US); Bethany K. Johnson, Midland, MI (US); Mike Ferritto, Midland, MI (US); Jodi Mecca, Midland, MI (US); Helene Dihang, Taisnières-sur-Hon (FR); Isabelle Van Reeth, Incourt Walloon Brabant (BE)

(73) Assignees: Rohm and Haas Company, Collegeville, PA (US); Dow Silicones Corporation, Midland, MI (US); Union Carbide Corporation, Midland, TX (US)

( * ) Notice: Subject to any disclaimer, the term of this patent is extended or adjusted under 35 U.S.C. 154(b) by 445 days.

This patent is subject to a terminal disclaimer.

(21) Appl. No.: 17/770,204

(22) PCT Filed: Nov. 18, 2020

(86) PCT No.: PCT/US2020/060979
§ 371 (c)(1),
(2) Date: Apr. 19, 2022

(87) PCT Pub. No.: WO2021/118775
PCT Pub. Date: Jun. 17, 2021

(65) Prior Publication Data
US 2022/0395447 A1    Dec. 15, 2022

Related U.S. Application Data

(60) Provisional application No. 62/947,593, filed on Dec. 13, 2019.

(51) Int. Cl.
| | | |
|---|---|---|
| A61K 8/73 | (2006.01) | |
| A61K 8/25 | (2006.01) | |
| A61K 8/34 | (2006.01) | |
| A61K 8/898 | (2006.01) | |
| A61Q 3/02 | (2006.01) | |
| A61Q 5/00 | (2006.01) | |

(52) U.S. Cl.
CPC .............. *A61K 8/731* (2013.01); *A61K 8/25* (2013.01); *A61K 8/34* (2013.01); *A61K 8/898* (2013.01); *A61Q 3/02* (2013.01); *A61Q 5/00* (2013.01); *A61K 2800/42* (2013.01); *A61K 2800/51* (2013.01)

(58) Field of Classification Search
None
See application file for complete search history.

(56) References Cited

U.S. PATENT DOCUMENTS

| | | |
|---|---|---|
| 5,583,244 A | 12/1996 | Uchida et al. |
| 6,703,027 B2 | 3/2004 | Kurosawa et al. |
| 6,726,917 B2 | 4/2004 | Kanji et al. |
| (Continued) | | |

FOREIGN PATENT DOCUMENTS

| | | |
|---|---|---|
| JP | 2007314655 A | 12/2007 |
| JP | 2008105994 A | 5/2008 |
| (Continued) | | |

OTHER PUBLICATIONS

Sibilia, "A Guide to Materials Characterization and Chemical Analysis", 1988, pp. 81-84.
(Continued)

*Primary Examiner* — Kyung S Chang
(74) *Attorney, Agent, or Firm* — Amy J Lanphierd

(57) ABSTRACT

A personal care composition is provided, including: a cosmetically acceptable carrier; and a silicon glycan of formula (I):

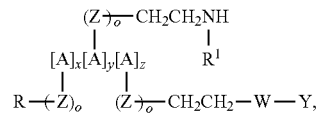

wherein each A comprises an independently selected saccharide moiety; wherein each W is an independently selected beta-amino alcohol moiety; wherein each Y comprises an independently selected organosilicon moiety; wherein each R is independently selected from substituted or unsubstituted hydrocarbyl groups, ether moieties, amine moieties, and H; wherein each $R^1$ is independently selected from substituted or unsubstituted hydrocarbyl groups and H; wherein each Z is an independently selected ether moiety; wherein each subscript a is independently 0 or 1; wherein subscripts x and y are each independently from $\geq 0$ to <1; wherein subscript z is selected from >0 to 1; with the proviso that x+y+z=1; and wherein moieties indicated by subscripts x, y, and z may be in randomized or block form in the silicon glycan.

6 Claims, No Drawings

(56) References Cited

U.S. PATENT DOCUMENTS

| | | | |
|---|---|---|---|
| 8,709,390 B2 | 4/2014 | Arisz et al. | |
| 8,790,627 B2 | 7/2014 | Erazo-Majewicz et al. | |
| 2006/0233736 A1* | 10/2006 | Meyers | A61Q 19/08 424/70.23 |
| 2013/0149269 A1 | 6/2013 | Delvalle et al. | |
| 2014/0357884 A1 | 12/2014 | Joffre et al. | |
| 2016/0081904 A1 | 3/2016 | Konishi et al. | |

FOREIGN PATENT DOCUMENTS

| | | | |
|---|---|---|---|
| WO | 2002092048 | 11/2002 | |
| WO | 2012027144 A1 | 3/2012 | |
| WO | 2013109523 A1 | 7/2013 | |
| WO | 2015066199 | 5/2015 | |
| WO | 2020142344 A1 | 7/2020 | |
| WO | WO-2021101679 A1 * | 5/2021 | C08B 11/145 |

OTHER PUBLICATIONS

Wagner, "Silicon-modified carbohydrate surfactants. II. Siloxanyl moieties containing branched structures", Applied Organometallic Chemistry, 1996, vol. 10, No. 6, pp. 437-450.

Search Report from corresponding Chinese Application No. 202080082859.5 dated Jul. 25, 2023.

* cited by examiner

PERSONAL CARE COMPOSITION COMPRISING A SILICON GLYCAN

The present invention relates to a personal care composition. In particular, the present invention relates to personal care composition, comprising: a cosmetically acceptable carrier; and a silicon glycan of formula (I):

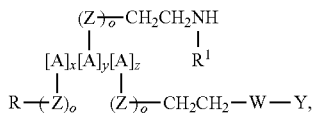

wherein each A comprises an independently selected saccharide moiety; wherein each W is an independently selected beta-amino alcohol moiety; wherein each Y comprises an independently selected organosilicon moiety; wherein each R is independently selected from substituted or unsubstituted hydrocarbyl groups, ether moieties, amine moieties, and H; wherein each $R^1$ is independently selected from substituted or unsubstituted hydrocarbyl groups and H; wherein each Z is an independently selected ether moiety; wherein each subscript a is independently 0 or 1; wherein subscripts x and y are each independently from $\geq 0$ to <1; wherein subscript z is selected from >0 to 1; with the proviso that x+y+z=1; and wherein moieties indicated by subscripts x, y, and z may be in randomized or block form in the silicon glycan.

Thickeners are commonly used in personal care compositions. Thickeners that are both suitable for use in personal care compositions as thickeners but that also provide additional benefits to formulators are in increasing demand. Of particular interest are effective thickeners that may be biosourced materials, that effectively thicken and also function to provide, for example, enhanced water repellancy/resistance, sensory benefits and/or salt resistance.

One category of biosourced thickeners for use in personal care compositions is described by Arisz et al. in U.S. Pat. No. 8,709,390. Arisz et al. disclose a non-uniformly substituted ("blocky") hydroxyethylcelluloses (HECs) and derivatives thereof that are asserted to exhibit associative behavior in both neat solutions and in filled systems. Arisz et al. posit that their HEC derivatives exhibit unique and highly desirable rheology and are said to be more efficient in thickening aqueous systems than prior art HEC products. The blocky HECs are asserted to be different from the prior art HEC products by having an unsubstituted anhydroglucose trimer ratio (U3R) greater than 0.21 and the hydroxyethyl molar substitution greater than about 1.3 and less than about 5.

Notwithstanding, there remains a need for effective thickeners that may preferably also function to provide secondary benefits for the end use personal care application, for example, enhanced water repellency/resistance, formulation clarity, sensory benefits and/or salt resistance.

The present invention provides a personal care composition, comprising: a cosmetically acceptable carrier; and a silicon glycan of formula (I):

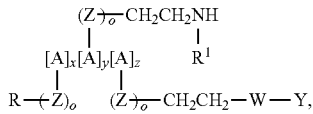

wherein each A comprises an independently selected saccharide moiety; wherein each W is an independently selected beta-amino alcohol moiety; wherein each Y comprises an independently selected organosilicon moiety; wherein each R is independently selected from substituted or unsubstituted hydrocarbyl groups, ether moieties, amine moieties, and H; wherein each $R^1$ is independently selected from substituted or unsubstituted hydrocarbyl groups and H; wherein each Z is an independently selected ether moiety; wherein each subscript a is independently 0 or 1; wherein subscripts x and y are each independently from $\geq 0$ to <1; wherein subscript z is selected from >0 to 1; with the proviso that x+y+z=1; and wherein moieties indicated by subscripts x, y, and z may be in randomized or block form in the silicon glycan.

The present invention provides a method of treating skin, nails or hair of a mammal, comprising: providing a personal care composition according to the present invention; and applying the personal care composition to at least one of skin, nails or hair of a mammal.

DETAILED DESCRIPTION

We have surprisingly found that the silicon glycans of the present invention function effectively as rheology modifiers/film-formers in personal care compositions (particularly in aqueous formulations); while also providing additional benefits for the desired enduse application. For example, providing effective thickening for aqueous hair styling formulations, while also imparting styling benefits (e.g., curl hold, humidity resistance); providing effective thickening for skin care or color cosmetic formulations while also imparting surface hydrophobicity for long wear applications; providing effective thickening for skin moisturizing applications, while also exhibiting high salt resistance (enabling higher salt formulations).

Unless otherwise indicated, ratios, percentages, parts, and the like are by weight.

As used herein, unless otherwise indicated, the phrase "molecular weight" or $M_W$ refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "cosmetically acceptable" as used herein and in the appended claims refers to ingredients typically used in personal care compositions, and is intended to underscore that materials that are toxic when present in the amounts typically found in personal care compositions are not contemplated as part of the present invention.

Preferably, the personal care composition of the present invention is selected from the group consisting of cosmetics (e.g., foundations, eye shadows, mascaras, lipsticks, blushes, pencils, etc.); skin lotions and creams; sun care products (e.g., lotions, creams, self-tanners, anhydrous formulations); antiaging products; antiperspirant and deodorants; a hair care formulations (e.g., styling gels, conditioners, conditioning shampoos, colorants); body washes (e.g., moisturizing body washes); nail care formulations, a pet care formulations. More preferably, a hair care formulation. Most preferably, a hair styling formulation.

Preferably, the personal care composition of the present invention, comprises: a cosmetically acceptable carrier (preferably, wherein the personal care composition comprises 10 to 99 wt % (preferably, 20 to 98.5 wt %; more preferably, 50 to 98 wt %; most preferably, 70 to 97 wt %), based on weight of the personal care composition, of the cosmetically acceptable carrier); and a silicon glycan (preferably, wherein the personal care composition comprises 0.1 to 20 wt % (preferably, 0.2 to 15 wt %; more preferably, 0.5 to 10 wt %; most preferably, 1 to 5 wt %), based on weight of the personal care composition, of silicon glycan) of formula (I):

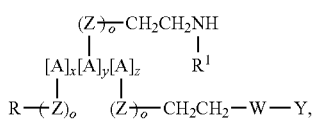

wherein each A comprises an independently selected saccharide moiety; wherein each W is an independently selected beta-amino alcohol moiety; wherein each Y comprises an independently selected organosilicon moiety; wherein each R is independently selected from substituted or unsubstituted hydrocarbyl groups, ether moieties, amine moieties, and H; wherein each $R^1$ is independently selected from substituted or unsubstituted hydrocarbyl groups and H; wherein each Z is an independently selected ether moiety; wherein each subscript a is independently 0 or 1; wherein subscripts x and y are each independently from $\geq 0$ to $<1$; wherein subscript z is selected from $>0$ to 1; with the proviso that x+y+z=1; and wherein moieties indicated by subscripts x, y, and z may be in randomized or block form in the silicon glycan.

Preferably, the personal care composition of the present invention, comprises a cosmetically acceptable carrier. More preferably, the personal care composition of the present invention, comprises 10 to 99 wt % (preferably, 20 to 98.5 wt %; more preferably, 50 to 98 wt %; most preferably, 70 to 97 wt %), based on weight of the personal care composition, of a cosmetically acceptable carrier. Most preferably, the personal care composition of the present invention, comprises 10 to 99 wt % (preferably, 20 to 98.5 wt %; more preferably, 50 to 98 wt %; most preferably, 70 to 97 wt %), based on weight of the personal care composition, of a cosmetically acceptable carrier; wherein the cosmetically acceptable carrier is selected to be capable of evaporating upon application of the personal care composition to mammalian skin, hair or nails (preferably, human skin, hair or nails; more preferably, human skin or hair; most preferably, human hair).

Preferably, the personal care composition of the present invention, comprises 10 to 99 wt % (preferably, 20 to 98.5 wt %; more preferably, 50 to 98 wt %; most preferably, 70 to 97 wt %), based on weight of the personal care composition, of a cosmetically acceptable carrier; wherein the cosmetically acceptable carrier is selected from the group consisting of water (e.g., deionized, distilled water); emulsions (e.g., oil-in-water emulsion, water-in-oil emulsion); alcohols (e.g., $C_{1-4}$ straight or branched chain alcohols such as methyl alcohol, ethyl alcohol, propyl alcohol, isopropyl alcohol, butyl alcohol); glycols (e.g., ethylene glycol, propylene glycol, butylene glycol, pentylene glycol, hexylene glycol, dipropylene glycol, ethoxydiglycol); glycerin; acetone; methyl acetate; butyl cellosolve and mixtures thereof. More preferably, the personal care composition of the present invention, comprises 10 to 99 wt % (preferably, 20 to 98.5 wt %; more preferably, 50 to 98 wt %; most preferably, 70 to 97 wt %), based on weight of the personal care composition, of a cosmetically acceptable carrier; wherein the cosmetically acceptable carrier includes water (preferably, at least one of deionized water and distilled water; more preferably, deionized, distilled water). Most preferably, the personal care composition of the present invention, comprises 10 to 99 wt % (preferably, 20 to 98.5 wt %; more preferably, 50 to 98 wt %; most preferably, 70 to 97 wt %), based on weight of the personal care composition, of a cosmetically acceptable carrier; wherein the cosmetically acceptable carrier is water (preferably, at least one of deionized water and distilled water; more preferably, deionized, distilled water).

Preferably, the personal care composition of the present invention, comprises a silicon glycan. More preferably, the personal care composition of the present invention, comprises 0.1 to 20 wt % (preferably, 0.2 to 15 wt %; more preferably, 0.5 to 10 wt %; most preferably, 1 to 5 wt %), based on weight of the personal care composition, of a silicon glycan. Most preferably, the personal care composition of the present invention, comprises 0.1 to 20 wt % (preferably, 0.2 to 15 wt %; more preferably, 0.5 to 10 wt %; most preferably, 1 to 5 wt %), based on weight of the personal care composition, of a silicon glycan; wherein the silicon glycan is of formula (I)

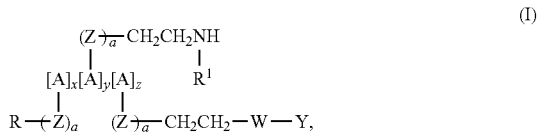

where each A comprises an independently selected saccharide moiety; each W is an independently selected beta-amino alcohol moiety; each Y comprises an independently selected organosilicon moiety; each R is independently selected from substituted or unsubstituted hydrocarbyl groups, ether moieties, amine moieties, and H; each $R^1$ is independently selected from substituted or unsubstituted hydrocarbyl groups and H; each Z is an independently selected ether moiety; each subscript a is independently 0 or 1; subscripts x and y are each independently from $\geq 0$ to $<1$; subscript z is from $>0$ to 1, with the proviso that x+y+z=1; and moieties indicated by subscripts x, y, and z may be in randomized or block form in the silicon glycan.

Preferably, the silicon glycan comprises a glycoside (i.e., at least two saccharides bound to one another via a glycosidic linkage) represented in the portion of formula (I) corresponding to the following moiety (i.e., the "glycoside moiety"):

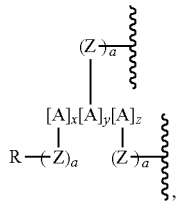

where each saccharide moiety A comprises, alternatively consists essentially of, a saccharide, and subscripts x, y, and z each represent a mole fractions of particular saccharide moieties A within the glycoside moiety. Said differently, each saccharide moiety A is bound to at least one other saccharide moiety A (e.g. via glycosidic linkage), such that each saccharide moiety A is a component of, and collectively form, the glycoside of the silicon glycan. Moreover, each saccharide moiety A indicated by subscripts x, y, and z may be in randomized or block form in the silicon glycan. As described in further detail herein, Z and R represent substituents native to or otherwise appended to each saccharide moiety A within the glycoside moiety of the silicon glycan.

It is to be appreciated that the term "saccharide" may be used synonymously with the term "carbohydrate" under general circumstances, and terms like "sugar" under more specific circumstances. The nomenclature of any particular saccharide is not exclusionary with regard to the composition of the silicon glycan as a whole, or any saccharide moiety A in particular. Rather, as will be understood by those of skill in the art, each saccharide moiety A may include, alternatively may be, any moiety that can be described as a saccharide, carbohydrate, sugar, starch, cellulose, and the like, or a derivative or modification thereof, or combinations thereof. Likewise, any combination of more than one A in the silicon glycan may be described more descriptive terms. For example, the term "polysaccharide" may be used synonymously with the term "glycoside," where both terms generally refer to a combination of more than one saccharide moiety A in the silicon glycan (e.g. where the combination of saccharide moieties A are linked together via glycosidic linkage(s) and collectively form the glycoside moiety). One of skill in the art will appreciate that terms such as "starch" and "cellulose" may be used to refer to such combinations of saccharide moieties A under specific circumstances (e.g. when a combination of more than one A in the silicon glycan A conforms to the structure known in the art as a "starch" or a "cellulose", etc.).

As introduced above, subscripts x, y, z each represent a mole fraction of particular saccharide moieties A within the glycoside moiety of the silicon glycan. As such, the values of $x+y+z=1$. More specifically, as represented by formula (I), not every saccharide moiety A within the glycoside moiety of the silicon glycan need be substituted identically. As such, the glycoside moiety of the silicon glycan may be described in various ways, e.g. in terms of overall composition using the mole fractions x, y, and z, in terms of the mean average number of substitutions per saccharide moiety A (i.e., the degree of substitution (DS), as understood by those of skill in the art), or combinations thereof.

Subscript x is a mole fraction of from $\geq 0$ to $<1$ (preferably, 0 to 0.99; more preferably, 0.1 to 0.99; more preferably, 0.3 to 0.99; more preferably, 0.5 to 0.99; more preferably, 0.6 to 0.99; more preferably, 0.7 to 0.99; more preferably, 0.7 to 0.9; more preferably, 0.7 to 0.85).

Subscript y is a mole fraction of from $\geq 0$ to $<1$ (preferably, 0 to 0.9; more preferably, 0.001 to 0.7; more preferably, 0.001 to 0.5; more preferably, 0.002 to 0.5; more preferably, 0.002 to 0.4; more preferably, 0.002 to 0.3; more preferably, 0.005 to 0.3; more preferably, 0.01 to 0.25).

Subscript z is a mole fraction of from $\geq 0$ to 1 (preferably, 0.00001 to 0.9; more preferably, 0.00001 to 0.7; more preferably, 0.00001 to 0.5; more preferably, 0.00001 to 0.3; more preferably, 0.00001 to 0.2; more preferably, 0.00001 to 0.15; more preferably, 0.000015 to 0.15; more preferably, 0.00002 to 0.15; more preferably, 0.00002 to 0.1; more preferably, 0.00005 to 0.09; more preferably, 0.0001 to 0.09; more preferably, 0.0005 to 0.09; more preferably, 0.001 to 0.09).

Preferably, the silicon glycan of the present invention has average degree of substitution of 0.00001 to 0.99 (preferably, 0.00001 to 0.5; more preferably, 0.00001 to 0.2; more preferably, 0.00001 to 0.15; more preferably, 0.0001 to 0.5; more preferably, 0.0001 to 0.2; more preferably, 0.0001 to 0.15) organosilicon moieties per saccharide moiety A.

The degree of aminoethyl substitution of the aminoethyl polysaccharide (A) can be determined by various techniques known by those of skill in the art. For example, the nitrogen content of the aminoethyl polysaccharide (A) (e.g. as determined via the Kjeldahl method) may be utilized directly, or adjusted (e.g. based on the nitrogen content of the hydroxyl-functional polysaccharide (A1)) to ascertain the degree of aminoethyl substitution the aminoethyl polysaccharide (A).

Regardless of the particular proportions described by subscripts x and y and z, the total number of saccharide moieties A in the silicon glycan (e.g. the degree of polymerization thereof) is preferably 10 to 10,000 (more preferably, 100 to 8,000; more preferably, 250 to 6,000; most preferably, 400 to 3,600).

Each saccharide moiety A may be the same as or different from any other saccharide moiety A in the silicon glycan. Examples of particular saccharides suitable for saccharide moiety A include those conventionally referred to as monosaccharides and/or sugars. Such monosaccharides include pentoses (i.e., furanoses), such as riboses, xyloses, arabinoses, lyxoses, fructoses, etc., and hexoses (i.e., pyranoses), such as glucoses, galactoses, mannoses, guloses, idoses, taloses, alloses, altroses, etc. One of skill in the art will appreciate that the glycoside moiety of the silicon glycan may comprise a disaccharide (e.g. a sucrose, a lactose, a maltose, a trehalose, etc.), an oligosaccharide (e.g. a malto-oligosaccharide, such as a maltodextrin, a rafinose, a stachyose, a fructooligosaccharides, etc.), a polysaccharide (e.g. a cellulose, a hemicellulose, a pectin, a glycogen, a hydrocolloid, a starch such as an amylose, an amylopectin, a modified starch, etc.), or the like, or combinations thereof.

Preferably, the silicon glycan comprises at least one saccharide moiety A that is a hexose. More preferably, the silicon glycan comprises at least one saccharide moiety A that is a hexose of formula:

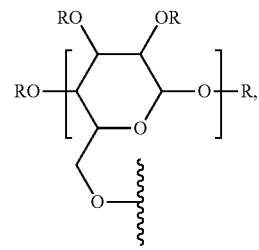

which, as understood by those of skill in the art, encompasses both internal as well as terminal monomers of the glycoside moiety formed therewith. Preferably, wherein each R is independently selected and as described herein. Preferably, the glycoside moiety of the silicon glycan comprises, alternatively consists essentially of, glucose monomers, and thus corresponds to formula:

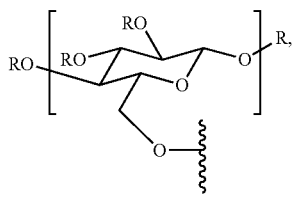

which, as understood by those of skill in the art, also encompasses both internal as well as terminal monomers of the glycoside moiety formed therefrom. Preferably, wherein each R is independently selected and as described herein.

Preferably, the glycoside moiety of the silicon glycan comprises a polysaccharide selected from pullulans, mannans, galactomannans, xyloglucans, xanthans, hydroxyethyl celluloses, carboxymethyl celluloses, ethyl hydroxyethyl celluloses, hydroxyethyl methyl celluloses, hydroxypropyl methyl celluloses, methyl celluloses, ethyl celluloses, and the like, as well as combinations thereof. More preferably, the glycoside moiety of the silicon glycan is a cellulose selected from the group consisting of hydroxyethyl cellulose, carboxymethyl cellulose, ethyl hydroxyethyl cellulose, hydroxyethyl methyl cellulose, hydroxypropyl methyl cellulose, methyl cellulose, ethyl cellulose and combinations thereof. Most preferably, the glycoside moiety of the silicon glycan is a hydroxyethyl cellulose.

Preferably, the glycoside moiety of the silicon glycan comprises a derivative (e.g. a modified and/or altered version) of one of the oligosaccharides or polysaccharides defined above. For example, the glycoside moiety may be a hydrophobically modified polysaccharide, a cationically modified polysaccharide, a hydrophilically modified polysaccharide a copolymerized polysaccharide, or a combination thereof. Such modifications typically alter the saccharide moieties A within the glycoside by appending substituents thereto (e.g. via the native hydroxyl moieties thereof, such as those at positions C2, C3, and/or C6 when the saccharide moieties A comprises a hexose). In particular, as introduced and shown above with respect to formula (I), the saccharide moieties A designated by subscript x of the silicon glycan comprise substituents R, and optionally Z, as described below. For example, R may be H in any saccharide moieties A designated by subscript x in the glycoside moiety. R is preferably H in each native (i.e., naturally occurring and/or unsubstituted) saccharide in any particular saccharide moiety A, such that the particular saccharide moiety A has at least one free hydroxyl substituent.

When the glycoside moiety of the silicon glycan comprises a polysaccharide derivative as described above, at least one R is selected from substituted or unsubstituted hydrocarbyl groups, ether moieties, and amine moieties. However, the silicon glycan may comprise any number of substituents R so defined, limited only by saccharide moieties A of the glycoside moiety, the DS of the glycoside moiety, etc., as will be understood by those of skill in the art in view of the description herein.

With regard to hydrocarbyl groups of R, the term "substituted" describes hydrocarbon moieties where either one or more hydrogen atoms is replaced with atoms other than hydrogen (e.g. a halogen atom, such as chlorine, fluorine, bromine, etc.), a carbon atom within a chain of the hydrocarbon is replaced with an atom other than carbon (i.e., R includes one or more heteroatoms (oxygen, sulfur, nitrogen, etc.) within the chain, or both. As such, it will be appreciated that R includes hydrocarbon moieties that may have substituents in and/or on (i.e., appended to and/or integral with) carbon chains/backbones thereof, such that R may comprise or be an ether, an amine, etc.

Hydrocarbyl groups for R may independently be linear, branched, cyclic, or combinations thereof. Cyclic hydrocarbyl groups encompass aryl groups as well as saturated or non-conjugated cyclic groups. Cyclic hydrocarbyl groups may independently be monocyclic or polycyclic. Linear and branched hydrocarbyl groups may independently be saturated or unsaturated. One example of a combination of a linear and cyclic hydrocarbyl group is an aralkyl group. Examples of hydrocarbyl groups include alkyl groups, aryl groups, alkenyl groups, halocarbon groups, and the like, as well as derivatives, modifications, and combinations thereof. Examples of alkyl groups include methyl, ethyl, propyl (e.g. iso-propyl and/or n-propyl), butyl (e.g. isobutyl, n-butyl, tert-butyl, and/or sec-butyl), pentyl (e.g., isopentyl, neopentyl, and/or tert-pentyl), hexyl, dodecyl, hexadecyl as well as branched saturated hydrocarbon groups having from 6 to 18 carbon atoms. Examples of aryl groups include phenyl, tolyl, xylyl, naphthyl, benzyl, and dimethyl phenyl. Examples of alkenyl groups include vinyl, allyl, propenyl, isopropenyl, butenyl, isobutenyl, pentenyl, heptenyl, hexenyl, and cyclohexenyl groups. Examples of monovalent halogenated hydrocarbon groups (i.e., halocarbon groups) include halogenated alkyl groups, aryl groups, and combinations thereof. Examples of halogenated alkyl groups include the alkyl groups described above where one or more hydrogen atoms is replaced with a halogen atom such as F or Cl. Specific examples of halogenated alkyl groups include fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl, 2,2-difluorocyclopropyl, 2,3-difluorocyclobutyl, 3,4-difluorocyclohexyl, and 3,4-difluoro-5-methylcycloheptyl, chloromethyl, chloropropyl, 2-dichlorocyclopropyl, and 2,3-dichlorocyclopentyl groups, as well as derivatives thereof. Examples of halogenated aryl groups include the aryl groups described above where one or more hydrogen atoms is replaced with a halogen atom, such as F or Cl. Specific examples of halogenated aryl groups include chlorobenzyl and fluorobenzyl groups.

Preferably, R may comprise an ether moiety having the average formula $—(OC_nH_{2n})_m—$, where subscript n is independently selected from 2 to 4 in each moiety indicated by subscript m, and subscript m is from 1 to 200. Those skilled in the art readily understand that additional and/or alternative groups may exist in the ether moiety, which do not substantially diminish the utility or properties of the glycoside moiety of the silicon glycan. In certain embodiments Preferably, R may comprise a polyether having the formula $—(OC_2H_4)_q(OC_3H_6)_r(OC_4H_8)_s—$, where subscripts q, r, and s are each independently 0 to 200, with the proviso that $1 \leq q+r+s \leq 600$ and units indicated by subscripts q, r, and s may be in randomized or block form in the polyether. More preferably, each of subscripts q, r, and s are each independently 0 to 100 (preferably, 0 to 50; more preferably, 0 to 20). Still more preferably, subscripts q, r, and s are each independently selected such that $1 \leq q+r+s \leq 300$ (preferably, $1 \leq q+r+s \leq 200$; more preferably, $1 \leq q+r+s \leq 60$).

One of skill in the art will understand that the moieties indicated by subscripts m, q, r, and s above are oxyalkylene units, such that R comprises a polyoxyalkylene when any two or more such moieties are present therein. As such, R may be selected from polyoxyalkylene groups, i.e., moieties comprising multiple oxyalkylene units. Preferably, each the oxyalkylene units indicated by subscripts q, r, and s, where present in R, may independently be branched or linear.

Preferably, R may comprise an amine moiety, such as a tertiary amine moiety, a quaternary ammonium moiety (e.g. a trimethylammonium moiety), or combinations thereof. Tertiary amines have the formula —NR'$_2$, where each R' is independently selected from substituted and unsubstituted hydrocarbyl groups and ether moieties (e.g. any of the hydrocarbyl groups and ether moieties described herein), or where each R' is part of, and together form, a cyclic moiety such that the amine moiety comprises a heterocycle (e.g. an N-substituted piperidine, morpholine, etc.). Cations of such tertiary amine moieties are protonated or alkylated forms thereof, having the general formula —[N(R')$_2$H]$^+$ or —[N(R')$_3$]$^+$ where each R' is independently selected and as defined above. Depending on the particular R' selected, the glycoside moiety of the silicon glycan may comprise and/or be defined as a N,N-diethylaminoethyl hydroxyethylcellulose, N,N-dimethylaminoethyl hydroxyethylcellulose, N,N-diisopropylaminoethyl hydroxyethylcellulose, N,N-dimethylaminopropyl hydroxyethylcellulose, N-ethyl piperidine hydroxyethylcellulose, N-ethyl morpholine hydroxyethylcellulose, N-ethyl pyrrolidine hydroxyethylcellulose, or combinations thereof.

It is to be appreciated that each R may be the same as or different from any other R in the silicon glycan. Moreover, each R may comprise the same or different functional moieties therein. For example, in certain embodiments, each R is selected from H and alkyl groups, where each alkyl group is optionally substituted (e.g. terminally and/or pendantly) with one or more of the tertiary amino moieties and/or the polyoxyalkylene groups described above. In these embodiments, each R may be said to be selected from substituted or unsubstituted hydrocarbyl groups, ether moieties, amine moieties, and H, where one of skill in the art will understand, in view of this description, that substituted hydrocarbyl groups suitable for R may comprise ether and/or amine moieties. In specific embodiments, each R is independently selected from H, $C_{1-18}$ hydrocarbyl groups, polyoxyalkylene groups, and tertiary amino groups.

The silicon glycan may comprise substituents Z. More specifically, with reference to formula (I), each subscript a is independently 0 or 1, such that each saccharide moiety A indicated by subscripts x, y, and z may independently be substituted with substituent Z, which is described in further detail below. In certain embodiments, the silicon glycan comprises at least one saccharide moiety A indicated by subscript x where subscript a is 1. In these or other embodiments, the silicon glycan comprises at least one saccharide moiety A indicated by subscript x where subscript a is 0. In these or other embodiments, the silicon glycan comprises at least one saccharide moiety A indicated by subscript y where subscript a is 1. In some such embodiments, subscript a is 1 in each moiety indicated by subscript y. In these or other embodiments, subscript a is 1 in each moiety indicated by subscript z, as will be understood in view of the description herein.

In general, each Z is a divalent linking group comprising an ether moiety (hereinafter referred to as the "ether moiety Z"). More specifically, each ether moiety Z is independently selected, and may be any ether moiety including at least one, alternatively at least two, ether groups. Each ether moiety Z may be the same as any or each other ether moiety Z. Preferably, the ether group(s) of each ether moiety Z have the formula —(C$_t$H$_{2t}$O)$_u$—, where subscript t is independently selected from 2 to 4 in each moiety indicated by subscript u, and subscript u is from 1 to 50 (preferably, 1 to 25; more preferably, 1 to 10; most preferably, 1 to 5). Preferably, subscript t is 2 and subscript u is 1, such that each ether moiety Z comprises an ethyl ether and the glycoside moiety of the silicon glycan may comprise and/or be defined as a hydroxyethyl cellulose.

In some embodiments, subscripts a and ether moieties Z may be collectively selected such that the glycoside moiety of the silicon glycan may comprise and/or be defined as a carboxymethyl cellulose, an ethyl hydroxyethyl cellulose, a hydroxyethyl methyl cellulose, a hydroxypropyl methyl cellulose, or the like, or combinations thereof. In view of these examples, one of skill in the art will appreciate that ether moiety Z may comprise groups in addition to the ether group(s), such as divalent hydrocarbon linking groups (e.g. methylene, ethylene, and propylene linking groups, etc.).

The glycoside moiety of the silicon glycan may include aminoethyl saccharide moieties. In particular, with reference to formula (I), the silicon glycan may comprise saccharide moieties A indicated by subscript y, which each include the aminoethyl moiety of sub-formula —CH$_2$CH$_2$N(H)R$^1$, where R$^1$ is a hydrocarbyl group or H. More specifically, each R$^1$ is independently selected from substituted or unsubstituted hydrocarbyl groups and H. Examples of suitable hydrocarbyl groups include those described above with respect to substituent R. In certain embodiments, each R$^1$ is independently selected from H and alkyl groups, such that, when R$^1$ is alkyl, the aminoethyl moiety is further defined as an N-alkyl aminoethyl moiety. In particular embodiments, each R$^1$ is the same as one another. For example, in some such embodiments, each R$^1$ is H or a $C_{1-4}$ hydrocarbyl group. In specific embodiments, each R$^1$ is H. In some embodiments, each R$^1$ is ethyl or methyl.

In certain embodiments, some of the aminoethyl moieties are protonated, and thus of the sub-formula —CH$_2$CH$_2$—[N(H$_2$)R$^1$]$^+$. The proportion of protonated aminoethyl moieties in the silicon glycan is limited only by the degree of aminoethyl substitution, and may be selected by one of skill in the art (e.g. during preparation of the silicon glycan, after preparation of the silicon glycan by combining an acid therewith, etc.).

With continued reference to formula (I), and as introduced above, the saccharide moieties A indicated by subscript z comprise a moiety of sub-formula —CH$_2$CH$_2$—W—Y, where W is a divalent beta-amino alcohol moiety (hereinafter the "beta-amino alcohol moiety W") and Y comprises an organosilicon moiety (hereinafter the "organosilicon moiety Y").

Each beta-amino alcohol moiety W is independently selected, such that any beta-amino alcohol moiety W may be the same as or different from any other beta-amino alcohol moiety W present in the silicon glycan. In particular, each beta-amino alcohol moiety W may be linear or branched with respect to the position of the alcohol group thereof, and may be protonated or unprotonated at the amine group (i.e., contain an amine or an ammonium cation). For example, each beta-amino alcohol moiety W is independently of one of the following formulas:

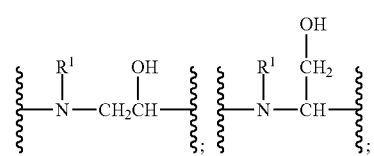

-continued

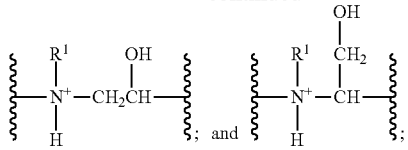

where each $R^1$ is independently selected and as defined above.

Each organosilicon moiety Y is independently selected, such that each organosilicon moiety Y may be the same as any or each other organosilicon moiety Y. In certain embodiments, each organosilicon moiety Y is the same as at least one, alternatively each, other organosilicon moiety Y. The organosilicon moiety Y is not generally limited in terms of structure and/or composition, and may be any moiety comprising at least one, alternatively at least two, organosilicon groups. For example, the organosilicon moiety Y may comprise an organosilyl group, an organosiloxane group, or combinations thereof. In certain embodiments, the organosilicon moiety Y is itself considered an organosilicon group.

In some embodiments, at least one, alternatively at least two, alternatively each organosilicon moiety Y comprises, alternatively is, a silane moiety. In such embodiments, the silane moiety typically has the general formula:

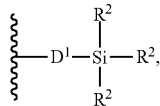

where $D^1$ is a divalent linking group; and each $R^2$ is independently selected from substituted or unsubstituted hydrocarbyl groups, alkoxy groups, and siloxy groups.

In general, $D^1$ is independently selected in each silane moiety present in any organosilicon moiety Y. Preferably, $D^1$ is selected from divalent substituted or unsubstituted hydrocarbon groups, which may optionally be modified or substituted, e.g. with alkoxy, siloxy, silyl, amino, amido, acetoxy, and aminoxy groups. $D^1$ may be linear or branched. When branched, $D^1$ may optionally be bonded (e.g. cross-linked) to a siloxane segment or a silane moiety (i.e., other than the silane represented by the sub-formula —$SiR^2_3$ in the general silane moiety formula above. In some embodiments, $D^1$ is a $C_{1-20}$ hydrocarbon group. However, $D^1$ may be a hydrocarbon groups comprising a backbone having at least one heteroatom (e.g. O, N, S, etc.). For example, in some embodiments, $D^1$ is a hydrocarbon having a backbone comprising an ether moiety.

Each $R^2$ is independently selected, and may be linear, branched, cyclic, or combinations thereof. While independently selected from substituted or unsubstituted hydrocarbyl groups, alkoxy and siloxy groups, each $R^2$ may comprise a combination thereof, such as a combination of hydrocarbyl groups and siloxy groups, as will be appreciated from the description herein. Examples of suitable substituted or unsubstituted hydrocarbyl groups for use as $R^2$ are set forth above with respect to R of general formula (I). Examples of suitable alkoxy groups include those having the general formula —O—R, where R is as defined above. Specific examples of suitable alkoxy groups include methoxy, ethoxy, propoxy, butoxy, phenoxy, etc. Examples of suitable siloxy groups include [M], [D], [T], and [Q] units, which, as understood in the art, each represent structural units of individual functionality present in organopolysiloxanes. More specifically, [M] represents the monofunctional unit of general formula $R^3_3SiO_{1/2}$; [D] represents the difunctional unit of general formula $R^3_2SiO_{2/2}$; [T] represents the trifunctional unit of general formula $R^3SiO_{3/2}$; and [Q] represents the tetrafunctional unit of general formula $SiO_{4/2}$, as shown by the general structural moieties below:

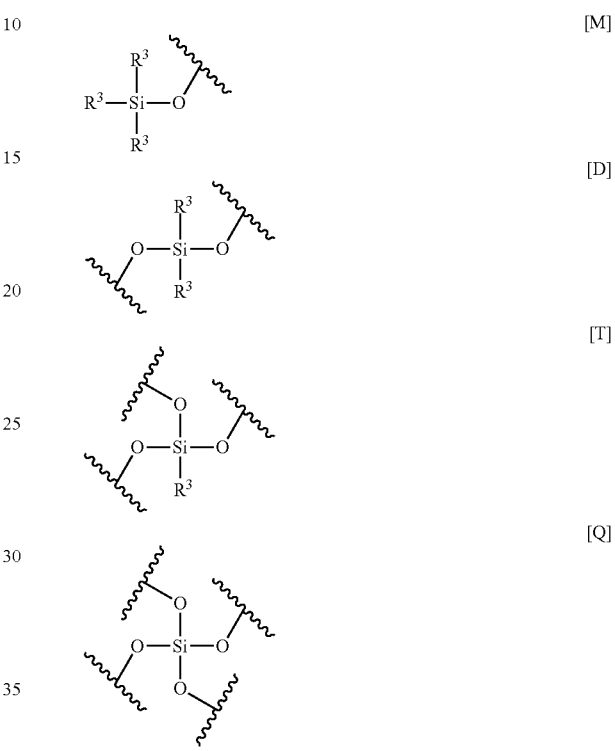

In these general structural moieties, each $R^3$ is independently a monovalent or polyvalent substituent. As understood in the art, specific substituents suitable for each $R^3$ are not limited, and may be monoatomic or polyatomic, organic or inorganic, linear or branched, substituted or unsubstituted, aromatic, aliphatic, saturated or unsaturated, and combinations thereof.

Preferably, each $R^3$ is independently selected from hydrocarbyl groups and siloxy groups. The hydrocarbyl group(s) represented by $R^3$, when present, may be substituted or unsubstituted, and may be aliphatic, aromatic, cyclic, alicyclic, etc., as described above with respect to the examples of hydrocarbyl groups suitable for R, which are equally exemplary of those suitable for use with respect to $R^3$. The siloxy group(s) represented by $R^3$, when present, may be substituted or unsubstituted, and may comprise, alternatively may be, any combination of [M], [D], [T], and [Q] units (i.e., the silane moiety may comprise a branched and/or dendrimeric siloxane).

In some embodiments, at least one, alternatively at least two, alternatively each organosilicon moiety Y of the silicon glycan comprises, alternatively is, an organopolysiloxane. In such embodiments, the organopolysiloxane typically has the formula:

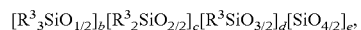

where each $R^3$ is as defined above, with the proviso that at least one $R^3$ is a silicon-bonded divalent linking group bonded to the beta-amino alcohol moiety W; and subscripts b, c, d and e are each mole fractions such that a+b+c+d=1, with the proviso that b+c+d>0.

It will be appreciated by those of skill in the art that the siloxy moieties indicated by subscripts b, c, d and e correspond to [M], [D], [T], and [Q] siloxy units, respectively, as introduced and described above. In some embodiments, the organopolysiloxane comprises repeating [D] units, i.e., where subscript c>0. In these embodiments, subscript b is typically a value of 0.3 to 1 (i.e., 0.3≤b≤1) (preferably, 0.3 to 0.9999; more preferably, 0.3 to 0.999; more preferably, 0.3 to 0.99; more preferably, 0.3 to 0.9; more preferably, 0.5 to 0.999; more preferably, 0.6 to 0.999; more preferably, 0.7 to 0.99; more preferably, 0.8 to 0.99; more preferably, 0.85 to 0.99; more preferably, 0.9 to 0.99). Subscript b is typically a value of 0 to 0.1 (i.e., 0≤a≤0.1) (preferably, 0 to 0.099; more preferably, 0 to 0.09; more preferably, 0 to 0.085; more preferably, 0 to 0.08; more preferably, 0 to 0.075; more preferably, 0 to 0.07; more preferably, 0 to 0.065; more preferably, 0 to 0.06; more preferably, 0 to 0.055; more preferably, 0 to 0.05; more preferably, 0.001 to 0.05; more preferably, 0.002 to 0.05; more preferably, 0.005 to 0.01). Subscripts d and e are typically each an independently selected value of 0 to 0.1 (i.e., 0≤d≤0.1 and 0≤e≤0.1) (preferably, 0 to 0.09; more preferably, 0 to 0.075; more preferably, 0 to 0.05; more preferably, 0 to 0.025; more preferably, 0 to 0.009; more preferably, 0 to 0.001; more preferably, 0 to 0.0001). In certain embodiments, the organopolysiloxane comprises a linear siloxane segment, where subscript c is 0.9 to 1, subscript b is 0 to 0.1, and subscripts d and e are each 0. When the organopolysiloxane comprises repeating [D] units, the number of specific [D] units (i.e., the degree of polymerization, DP) in any one siloxane segment is not limited. Typically, such siloxane segments comprise from 1 to 700 repeating [D] units (preferably, 2 to 600; more preferably, 2 to 500; more preferably, 5 to 400; more preferably, 5 to 300; more preferably, 10 to 250; more preferably, 10 to 200; more preferably, 15 to 150; more preferably, 15 to 100; more preferably, 15 to 50) repeating [D] units.

With respect to both the silane moiety and the organopolysiloxane described above (i.e., when either or both is utilized in or as the organosilicon moiety Y), the presence and proportion of [M], [D], [T], and [Q] units is independently selected, as is the particular substituent for each $R^3$ of each silyl substituent of the silane moiety as well as for each $R^3$ of any particular siloxy unit (e.g. those indicated by subscripts b, c, and d). For example, a proportion of [T] and [Q] units of or around 0 is typically selected to increase the linearity of the organopolysiloxane, such as when the organopolysiloxane is a linear organopolysiloxane. Such organopolysiloxanes are typically linear or substantially linear, but may include some branching attributable to [T] and/or [Q] units (e.g. where d+e>0). Conversely, the proportion of [T] and/or [Q] units is selected to be greater than 0 when the organopolysiloxane is a resin. Accordingly, one of skill in the art will select the composition of the siloxane segments to control the composition of the organopolysiloxane, and thus the silicon glycan, e.g. based on a desired property of a particular organopolysiloxane, a desired/intended property and/or characteristic (e.g. physical, chemical, aesthetic, etc.) of any of: the silicon glycan; a particular phase (e.g. a non-aqueous, continuous, and/or silicone phase) of an emulsion prepared therewith and/or the emulsion itself; a composition comprising the silicon glycan; a coating formed from such a composition; and combinations thereof. For example, it may be desirable for the silicon glycan to have a high melting temperature and/or softening point, or for a composition prepared therewith to be in a specific form (e.g. the form of a solid, gel, etc.), and selecting the composition of the organopolysiloxane of the silicon glycan may allow one of skill in the art to achieve a range of such desirable properties. In general, when linear siloxane segments are utilized in the organosilicon moiety Y, layers or coatings formed from compositions comprising the silicon glycan in accordance with the present disclosure will typically have improved feel (e.g. comfortable deposit) and flexibility as compared to embodiments where the organopolysiloxane includes increased branching attributable to [T] and/or [Q] units. When resinous organopolysiloxanes are used in or as the organosilicon moiety Y, products formed with/from the compositions comprising the silicon glycan in accordance with the present disclosure will typically have increased hardness and transfer resistance as compared to embodiments where more linear siloxane segments are utilized.

Methods of preparing silicon glycan as described herein are disclosed in commonly owned U.S. patent application Ser. No. 62/786,648, filed Dec. 31, 2018; incorporated herein by reference.

Preferably, the personal care composition of the present invention, further comprises at least one personal care active selected from the group consisting of an absorbent; an acid; an aesthetic modifier; an antiaging agent; an antidandruff agent; an antifoam agent; an antifrizz agent; an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); an antioxidant (e.g., butylated hydroxytoluene); an antiperspirant or deodorant active; an antistatic agent; a bioactive agent; a bleaching or coloration agent; a chelating agent (e.g., disodium EDTA, tetrasodium EDTA, citric acid, lactic acid); a cleansing surfactant; a conditioning agent (e.g., guar hydroxypropyltrimonium chloride, PQ-10, PQ-7); a colorant; a color ingredient; a consistency factor; a deodorant; an emulsifying agent (e.g. PEG-100 stearate & glyceryl stearate mixture); an emollient (polyoxyethylene glycol ($C_{7-20}$) fatty acid, esters of glycerol—e.g., PEG-7 glyceryl cocoate, PEG-30 glyceryl cocoate, PEG-12 glyceryl laureate, PEG-20 glyceryl oleate); a fat; a filler; a foaming agent; a fragrance; a hair oil; a hair treatment active; a hair waving/straightening agent; a hair styling agent; a hard particle; a humectant; a lecithin; a light management powder or particle; a lubricating agent; a moisturizer; a natural ingredient; an oil; an opacifier; a pearlizing agent; a penetrant; a pH adjusting agent; a phospholipid; a pigment; a plant extract; a polymer; a preservative; a protein/amino acid; a rheology modifier; a salt (e.g., sodium chloride, magnesium chloride); a sensory modifier; a silicone oil; a skin care active; a skin coolant; a skin protectant; a slip agent; an SPF booster (e.g., Sunsphere™ polymers) a soap; a soft particle; a stabilizer; a sun care active; a sunscreen additive; a super fatting agent; a surfactant; a thickener (e.g., polysaccharides, cellulosic polymers); a vitamin; a water proofing agent; a wax; and the like.

Preferably, the personal care composition of the present invention is a color cosmetic formulation and further comprises a color ingredient. More preferably, the personal care composition of the present invention is a color cosmetic formulation and further comprises a color ingredient; wherein the color ingredient is selected from the group consisting of inorganic pigments, organic pigments, aqueous pigment dispersions and mixtures thereof. Still more preferably, the personal care composition of the present invention is a color cosmetic formulation and further comprises a color ingredient; wherein the color ingredient is selected from the group consisting of Ext. D&C Yellow No. 2, Ext. D & C Violet No. 2, FD&C Red No. 4, FD&C Red No. 40, FD&C Yellow No. 5, FD&C Yellow No. 6, FD&C Green No. 3, FD&C Blue No. 1, D&C Yellow No. 7, D&C Yellow No. 8, D&C Yellow No. 10, D&C Yellow No. 11, D&C Violet No. 2, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 34, D&C Red No. 33, D&C Red No. 36, D&C Green No. 5, D&C Green No. 6, D&C Green No. 8, D&C Blue No. 4, D&C Orange No. 4, D&C Orange No. 5, D&C Orange No. 10, D&C Orange No. 11, D&C Brown No. 1, Aluminum powder, Annatto, Bismuth citrate, Bismuth Oxychloride, Bronze powder, Caramel, Carmine, (β-Carotene, Chromium hydroxide green, Chromium oxide green, Copper chlorophyllin, Copper powder, Dihydroxyacetone, Ferric Ammonium ferrocyanide, Ferric ferrocyanide, Guanine, Iron oxide, Manganese Violet, Mica, Silver, Titanium Dioxide, Ultramarine, Zinc Oxide, silicone dioxide and mixtures thereof. Still more preferably, the personal care composition of the present invention is a color cosmetic formulation and further comprises a color ingredient; wherein the color ingredient includes at least one iron oxide. Most preferably, the personal care composition of the present invention is a color cosmetic formulation and further comprises a color ingredient; wherein the color ingredient includes a mixture of iron oxides.

Preferably, the personal care composition of the present invention is a suncare formulation and further comprises a suncare active. More preferably, the personal care composition of the present invention is a suncare formulation and further comprises a suncare active; wherein the suncare active is a UV radiation absorbing agent. Still more preferably, the personal care composition of the present invention is a color cosmetic formulation and further comprises a suncare active; wherein the suncare active is a UV radiation absorbing agent selected from the group consisting of physical blockers (e.g., red petrolatum, titanium dioxide, zinc oxide) and chemical absorbers (e.g., 1-(4-methoxyphenol)-3-(4-tert-butylphenyl)propane-1,3-dione (INCI: Butyl Methoxydibenzoylmethane); 2-hydroxy-4-methoxybenzophenone (INCI: B enzophenone-3); dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenylacrylate; 2-ethylhexyl-2-cyano-3,3-diphenyl-2-propenoate (INCI: octocrylene); 2-ethylhexyl-2-hydroxybenzoate (INCI: Ethylhexyl Salicylate); homomenthyl salicylate; glyceryl aminobenzoate; triethanolamine salicylate; digalloyl trioleate; law sone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate (INCI: Homosalate). Yet more preferably, the personal care composition of the present invention is a suncare formulation and further comprises a suncare active; wherein the suncare active is a UV radiation absorbing agent comprises a mixture of UV radiation absorbing agents. Most preferably, the personal care composition of the present invention is a suncare formulation and further comprises a suncare active; wherein the suncare active is a UV radiation absorbing agent is a mixture of UV absorbing agents including at least one of titanium dioxide; zinc oxide; 1-(4-methoxyphenol)-3-(4-tert-butylphenyl)propane-1,3-dione; 2-ethylhexyl-2-hydroxybenzoate; 2-ethyhexyl-2-cyano-3,3-diphenyl-2-propenoate; 2-hydroxy-4-methoxybenzophenone and 3,3,5-trimethylcyclohexyl 2-hydroxybenzoate.

Preferably, the personal care composition of the present invention is an aqueous moisturizing formulation; wherein the cosmetically acceptable carrier comprises water (preferably, wherein the cosmetically acceptable carrier is water) and wherein the personal care composition further comprises a salt (preferably, wherein the composition viscosity is not reduced as a result of the salt incorporation). More preferably, the personal care composition of the present invention is an aqueous moisturizing formulation; wherein the cosmetically acceptable carrier comprises water (preferably, wherein the cosmetically acceptable carrier is water) and wherein the personal care composition further comprises a salt; wherein the salt is selected from the group consisting of sodium chloride, calcium chloride, magnesium chloride and mixtures thereof (preferably, wherein the composition viscosity is not reduced as a result of the salt incorporation). Still more preferably, the personal care composition of the present invention is an aqueous moisturizing formulation; wherein the cosmetically acceptable carrier comprises water (preferably, wherein the cosmetically acceptable carrier is water) and wherein the personal care composition further comprises at least 0.5 wt % (preferably, 1 to 10 wt %; more preferably, 1.5 to 8 wt %; still more preferably, 3 to 7 wt %; most preferably, 4 to 6 wt %), based on weight of the personal care composition, of a salt; wherein the salt is selected from the group consisting of sodium chloride, magnesium chloride and mixtures thereof (preferably, wherein the composition viscosity is not reduced as a result of the salt incorporation). Most preferably, the personal care composition of the present invention is an aqueous moisturizing formulation; wherein the cosmetically acceptable carrier comprises water (preferably, wherein the cosmetically acceptable carrier is water) and wherein the personal care composition further comprises at least 0.5 wt % (preferably, 1 to 10 wt %; more preferably, 1.5 to 8 wt %; still more preferably, 3 to 7 wt %; most preferably, 4 to 6 wt %), based on weight of the personal care composition, of a salt; wherein the salt is selected from the group consisting of sodium chloride, magnesium chloride and mixtures thereof (preferably, wherein the composition viscosity is not reduced as a result of the salt incorporation).

Preferably, the personal care composition of the present invention is an aqueous hair styling formulation; wherein the cosmetically acceptable carrier comprises water (preferably, wherein the cosmetically acceptable carrier is water) and wherein the personal care composition further comprises at least one of a chelating agent, an emollient and a preservative. More preferably, the personal care composition of the present invention is an aqueous hair styling formulation; wherein the cosmetically acceptable carrier comprises water (preferably, wherein the cosmetically acceptable carrier is water) and wherein the personal care composition further comprises a chelating agent, an emollient and a preservative. Most preferably, the personal care composition of the present invention is an aqueous hair styling formulation; wherein the cosmetically acceptable carrier comprises water (preferably, wherein the cosmetically acceptable carrier is water) and wherein the personal care composition further comprises a 0.001 to 1 wt %, based on weight of the personal care composition, of a chelating agent; 0.1 to 20 wt %, based on weight of the personal care composition, of an emollient; and 0.05 to 10 wt %, based on weight of the personal care composition, of a preservative.

Preferably, the personal care composition of the present invention optionally further comprise a chelating agent. More preferably, the personal care composition of the present invention further comprises 0.001 to 1 wt % (preferably, 0.03 to 0.25 wt %), based on weight of the personal care composition, of a chelating agent. Still more preferably, the personal care composition of the present invention further comprises 0.001 to 1 wt % (preferably, 0.03 to 0.25 wt %), based on weight of the personal care composition, of a chelating agent; wherein the chelating agent is selected from the group consisting of disodium ethylenediaminetetraacetic acid (EDTA), tetrasodium EDTA, citric acid, lactic acid and mixtures thereof. Most preferably, the personal care composition of the present invention further comprises 0.001 to 1 wt % (preferably, 0.03 to 0.25 wt %), based on weight of the personal care composition, of a chelating agent; wherein the chelating agent includes disodium EDTA.

Preferably, the personal care composition of the present invention optionally further comprises an antimicrobial agent/preservative. More preferably, the personal care composition of the present invention further comprises 0.05 to 10 wt % (preferably, 0.075 to 1 wt %; more preferably, 0.08 to 0.5 wt %), based on weight of the personal care composition, of an antimicrobial agent/preservative; wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Most preferably, the personal care composition of the present invention further comprises 0.05 to 10 wt % (preferably, 0.075 to 1 wt %; more preferably, 0.08 to 0.5 wt %), based on weight of the personal care composition, of an antimicrobial agent/preservative; wherein the antimicrobial/preservative is a mixture of phenoxyethanol and an isothiazolinone (more preferably, wherein the antimicrobial/preservative is a mixture of phenoxyethanol and methylisothiazolinone).

Preferably, the method of treating skin, hair or nails of a mammal of the present invention, comprises: providing a personal care composition of the present invention; applying the personal care composition to the skin, hair or nails hair of a mammal.

Preferably, the method of treading skin, hair or nails of a mammal of the present invention is a method of treating human skin, comprising: providing a personal care composition of the present invention; applying the personal care composition to human skin.

Preferably, the method of treading skin, hair or nails of a mammal of the present invention is a method of treating human hair, comprising: providing a personal care composition of the present invention; applying the personal care composition to human hair.

Preferably, the method of treading skin, hair or nails of a mammal of the present invention is a method of treating human nails, comprising: providing a personal care composition of the present invention; applying the personal care composition to human nails.

Some embodiments of the present invention will now be described in detail in the following Examples.

Example S1: Synthesis of Aminoethyl Modified Hydroxy Ethyl Cellulose

A 2000 ml four-necked round-bottomed flask was fitted with a rubber serum cap, a stirring paddle and motor, a nitrogen inlet, an immersion thermocouple connected to a J-KEM controller, and a Friedrich condenser bubbler. The flask was charged with 134.64 g of CELLOSIZE™ HEC AM-103 (available form The Dow Chemical Company) (F203G6U418, contained HEC=120.01 g, 0.48 moles with a mineral oil), 48.76 g (0.42 moles) of 2-chloroethylamine hydrochloride, and a diluent composition of 672.5 g of isopropyl alcohol and 76.2 g of water. The mixture was purged with nitrogen for one hour while stirring.

After the one hour nitrogen purge, 32.82 g (0.41 moles) of 50% aqueous sodium hydroxide was added to the mixture dropwise under nitrogen with stirring over a minute, and the mixture was allowed to stir for another 5 minutes under nitrogen. The slurry was then heated with a heating mantle to 80° C. using the J-KEM controller and held at that temperature for 4 hours with stirring under nitrogen.

The slurry was then cooled to room temperature and 3.0 g of glacial acetic acid were added. The polymer was recovered by vacuum filtration through a metal fitted Buchner funnel, and washed in the Buchner funnel: once with a mixture of 1200 g of acetone and 400 g of distilled water, three times with a mixture of 1200 g of acetone and 320 g of distilled water, once with a mixture of 1200 g of acetone and 160 g of distilled water, and twice with 1200 g of pure acetone. The polymer was recovered by vacuum filtration, briefly air dried, then dried overnight in vacuo at 50° C.

The polymer was manually ground using a mortar & pestle and screened through a #30 US standard sieve. The polymer was recovered as an off-white solid (140.52 g), with a volatiles content of 1.89%, an ash content of 6.06% (as sodium chloride), and a Kjeldahl nitrogen value of 1.98% corresponding to a CS of 0.42. The solution viscosity of a 2.0% aqueous solution (corrected for volatiles and ash) measured on the TA Instruments DHR-3 rheometer at 25.0° C. and a shear rate of 6.3 s$^{-1}$ was found to be 476 mPa-s.

The resulting cationic HEC (160.4 g, 0.565 mol, 1 equiv., amine DS=0.42) was suspended in 600 g of a 80/20 (by weight) isopropyl alcohol/water mixture in a 1000 ml three-necked flask equipped with a reflux condenser and a nitrogen inlet. The reaction mixture was flushed with nitrogen for one hour, then 18.4 g of a 50 wt % aqueous solution of sodium hydroxide was added at once. The solution mixture was heated to 70° C. for 4 hours, then the reaction mixture was left to cool naturally and stirred overnight.

The solution was filtered on a Buchner funnel with Whatman® #44 filter paper. The solids were removed, then placed back in the three neck flask and further stirred with an 80/20 isopropyl alcohol/water mixture for 4 hours. The solids were then filtered once again on a Buchner funnel with Whatman® #44 filter paper. The solids were rinsed with 600 ml of an 80/20 isopropyl alcohol/water mixture, 600 ml of a 90/10 isopropyl alcohol/water mixture, then 600 ml of pure isopropyl alcohol. The solids were then dried in a vacuum oven at 50° C. overnight.

Example S2: Synthesis of Silicon Modified Hydroxy Ethyl Cellulose

In a 1 liter three neck flask was added 100 g of neutralized aminoethyl modified HEC prepared according to Example 51 having an amine-DS (degree of substitution) of 0.42 along with 500 g of a 90/10 (by weight) 2-propanol/H$_2$O mixture. The siloxane MD$_{10}$D$_1$*M(100 g) was then added at once to the flask contents.

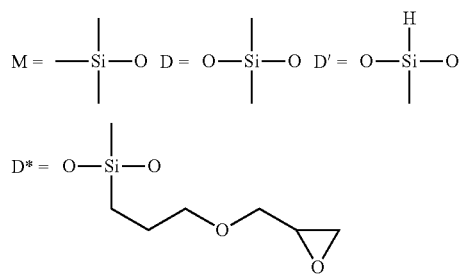

The flask contents were then heated to 80° C. for 15 hours. The resulting solids were then filtered on a Buchner funnel with Whatman® #44 filter paper. The recovered solids were rinsed with 350 mL of acetone, 350 mL of toluene, 350 mL of an 80/20 2-propanol/H$_2$O mixture, 350 mL of a 90/10 2-propaol/H$_2$O mixture, 350 mL of 2-propanol, 350 mL of toluene, then finally 2×350 mL of acetone. The product material was dried in a vacuum oven at 50° C. for 8 hours, then passed through a fine mesh filter. The particles that were too large to pass through the filter were ground with a mortar and pestle. An off-white powder (101.7 g) product was obtained. The product was analyzed by XRF, revealing a 1.28 wt % Si content.

Example S3: Synthesis of Silicon Modified Hydroxy Ethyl Cellulose

In a 1 liter three neck flask was added 58.1 g of neutralized aminoethyl modified HEC prepared in similar fashion to Example S1 but having an amine-DS (degree of substitution) of 0.3.68 along with 300 g of a 90/10 (by weight) 2-propanol/H$_2$O mixture. The siloxane MD$_1$*M (61.7 g) was then added at once to the flask contents.

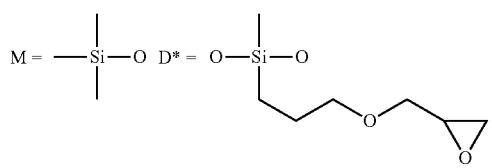

The flask contents were then heated to 70° C. for 3.75 hours. The resulting solids were filtered on a Buchner funnel with Whatman® #44 filter paper. The recovered solids were placed back into the 1 liter flask and 4.47 g of glacial acetic acid was added. The mixture was stirred for 15 minutes. The solids were again filtered on a Buchner funnel with Whatman® #44 filter paper. The solids were rinsed with 500 mL of acetone, 500 mL of toluene, 500 mL of an 80/20 2-propanol/H$_2$O mixture, 500 mL of a 90/10 2-propaol/H$_2$O mixture, 500 mL of 2-propanol, 500 mL of toluene, then finally 2×500 mL of acetone. The product solids were dried in a vacuum oven at 50° C. for 8 hours. An off-white powder product was obtained. The product was analyzed by XRF, revealing a 1.18 wt % Si content.

TABLE 1

Synthesis Summary

| Example | Backbone | Si Content XRF Si (wt %) | DS | Siloxane chain |
|---|---|---|---|---|
| Example S1 | AM-103[a] | 0 | 0 | — |
| Example S2 | AM-103[a] | 1.28 | 0.011 | MD$_{10}$D$_1$* (13 repeat Si—O—) |
| Example S3 | AM-103[a] | 1.18 | 0.04 | Me$_3$Si—O—Si—(Me)—O—SiMe$_3$ (3 repeat Si—O—) |

[a]CELLOSIZE ™ AM-103 hydroxy ethyl cellulose with a weight average molecular weight, M$_W$, of 370,000 from The Dow Chemical Company

Rheology Analysis

The rheology of a 1.0 wt % solution of the product from Example S3 in deionized water was studied using a TA Instruments DHR-3 rheometer with an aluminum cup and bob. The rehology response was measured by flow curve at 25.0° C., the frequency sweep (fixed torque at 11 mN-m) at 25.0° C., the stress sweep (fixed frequency at 0.5 Hz) at 25.0° C., and a thermal sweep (fixed torque at 10 mN-m and frequency at 0.5 Hz) from 25.0° C. to 100.0° C. The resulting frequency sweep showed a highly elastic fluid that exhibited little change over the frequency range tested. In most cellulose ethers (including hmHEC), the storage and loss modulus gradually increase with increasing angular frequency. In this case, with the silicon modified hydroxy ethyl cellulose of Example S3 there was little change in either the loss or storage moduli. The failure to show a significant increase in the storage modulus with increasing frequency suggests that the elastic response was more uniform (no change with frequency), which was confirmed by the phase angle.

Water Contact Angle Measurement

A separate 1.5 wt % water solution was prepared with each of unmodified HEC (AM 103), product prepared according to Example S2 and product prepared according to Example S3. A film was separately drawn down with each of the solutions on a Mylar film with a 6 mil bar film applicator. The films were allowed to dry overnight at room temperature. Each of the solutions yielded a clear/transparent film. Contact angle data was then acquired for each of the films using a Kruss DSA100 instrument. Water (6 drops)

was placed on each film separately and measured at time zero and 200 seconds. The resulting data are reported as the average and standard deviation in TABLE 2. Due to its hydrophilicity, the film prepared with the unmodified HEC (AM-103) had a low water contact angle, and it dropped 50% after 200 seconds. Introducing hydrophobic siloxane chains to the HEC backbone with a Si degree of substitution (DS) of 0.04 resulted in a significant increase in water contact angle observed. The films prepared using either the product from Example S2 or Example S3 exhibited a much higher initial water contact angle than the unmodified HEC, and a 4 times increase in water contact angle after 200 seconds. Such hydrophobicity is desirable in many personal care compositions where film formation with maintained film mechanical integrity when in contact with water over time is desirable (e.g., long wear cosmetics, sunscreens, hair styling formulations).

TABLE 2

| Treatment Polymer | Time (in seconds) | Water Contact Angle Avg. Measured | Std. dev. |
|---|---|---|---|
| AM-103[a] | 0 | 18.1 | 1.0 |
| | 200 | 8.2 | 0.8 |
| Example S2 | 0 | 45.2 | 3.5 |
| | 200 | 42 | 3.8 |
| Example S3 | 0 | 54.1 | 2.0 |
| | 200 | 40.5 | 3.8 |

[a]CELLOSIZE ™ AM-103 hydroxyethyl cellulose with a weight average molecular weight, $M_w$, of 370,000 from The Dow Chemical Company Comparative Examples CF1-CF2 And Example F1: Hair Gel Formulation Hair styling gels were prepared in each of Comparative Examples CF1-CF2 and Example F1 according to the formulations provided in TABLE 3. Phase A ingredients were first mixed with overhead agitation at room temperature until homogenous. In a separate container, phase B ingredients were first mixed and heated to 70° C. under agitation until clear. The phase B solution was then allowed to cool down to room temperature. Under high shear, phase B solution was then slowly added into the phase A ingredients until a clear and homogenous solution was obtained. The pH of the combined mixture was adjusted to 6-7 with citric acid (Phase C). Finally, the preservative (phase D) was added to the combined mixture under high agitation to provide the product hair gel formulations.

TABLE 3

| Phase | Ingredient INCI name | Formulations (in parts by weight, pbW) | | |
|---|---|---|---|---|
| | | CF1 (pbW) | CF2 (pbW) | F1 (pbW) |
| A | Deionized water | 49.60 | 49.60 | 50.50 |
| A | Ethyl acetate and cyclohexane[1] | 0.50 | 0.50 | — |
| A | Disodium EDTA[2] | 0.10 | 0.10 | 0.10 |
| A | Glycerin | 3.00 | 3.00 | 3.00 |
| B | Deionized Water | 44.00 | 44.00 | 44.00 |
| B | Commercial styling polymer[3] | 2.00 | — | — |
| B | AM-103[4] | — | 2.00 | — |
| B | Product of Example S3 | — | — | 2.00 |

TABLE 3-continued

| Phase | Ingredient INCI name | Formulations (in parts by weight, pbW) | | |
|---|---|---|---|---|
| | | CF1 (pbW) | CF2 (pbW) | F1 (pbW) |
| B | Triethanolamine, 99% | 0.40 | 0.40 | — |
| C | Citric acid | 0.40 | 0.40 | — |
| D | Preservative[5] | 0.10 | 0.10 | 0.10 |

[1]Available from Lubrizol under the tradename Carbopol 980.
[2]Available from The Dow Chemical Company under the tradename Versene NA.
[3]Available from Ashland under the tradename PVP K-90 polyvinylpyrrolidone.
[4]Available from The Dow Chemical Company under tradename CELLOSIZE ™ AM-103 hydroxyethyl cellulose
[5]Available from DuPont under tradename Kathon ™ CG.

Hair Treatment Performance Tests

Unless otherwise specified, the following hair treatment experiments were performed using 8 inch long, unbleached dark brown hair tresses (4 g) purchased from International Hair Importers & Products, Inc. Each tress was first rinsed in tap water for 30 seconds, washed with a 9 wt. % sodium lauryl sulfate (SLS; 0.2 g/g of hair) for 30 seconds, rinsed with tap water for 1 minute before treatment with one of the hair gel formulations prepared according to Comparative Examples CF1-CF2 and Example F1.

Each tress was treated by applying the hair gel formulation noted in TABLES 4-6 (0.4 g/g of hair) onto the hair tress and thoroughly rubbing onto the hair fibers for 2 minutes until a uniform coating over the tress was obtained. The hair tress was subsequently rolled onto a ⅝ inch curler in a concentric coil configuration. The hair coil was then secured on the curler with a bobby pin. The curled hair tresses were dried in a controlled temperature (25° C.) and relative humidity (50%) room overnight. The fully dried hair coils were gently taken off the curlers right before the subsequent application tests.

Curl Compression Test

Curl compression tests were conducted using Dia-Stron UV 1000 control Unit. The individual hair curls were clamped to a holder. 25% curl compression displacement was applied to the hair curl at a 200 mm/min rate, and the compression force was recorded by a transducer as a function of curl displacement. Five repeats were done on each hair curl. For each hair gel formulation, the test was conducted on two hair curls. The average peak compression force for the treated hair curls is provided in TABLE 4.

TABLE 4

| Formulation Example | Treatment Polymer | Peak Compression Force (gmf) |
|---|---|---|
| Comp. Example CF1 | Polyvinylpyrrolidone[1] | 152.35 |
| Comp. Example CF2 | hydroxyethylcellulose[2] | 200.46 |
| Example F1 | Example S3 | 439.47 |

[1]Available from Ashland under the tradename PVP K-90
[2]Available from The Dow Chemical Company under tradename CELLOSIZE ™ AM-103

Humidity Resistance Tests

The as prepared hair curls were hung in a rack and placed inside a humidity oven with a relative humidity of 90% at a temperature of 25° C. The length of the curls was measured at different time intervals, started from t=0. The test was performed in triplicate for each hair gel formulation. The percent curl retention was calculated using the formula:

$$\% \text{ curl retention} = \frac{L_0 - L_t}{L_0 - L_i} \times 100\%$$

wherein $L_o$, was the length of each uncurled hair tress (i.e., 8"); $L_i$ was the initial length of each hair curl before humidity oven exposure; and $L_t$ was the length of the hair curl after humidity oven exposure at a given time duration. The average percent curl retention for the treated hair curls is provided in TABLE 5.

TABLE 5

| Formulation Example | Treatment Polymer | % Curl Retention vs. Time (hrs) | | | | | |
|---|---|---|---|---|---|---|---|
| | | 0 | 0.5 | 1 | 2 | 4 | 8 |
| Comp. Example CF1 | Polyvinyl-pyrrolidone[1] | 100 | 27.5 | 20.0 | 14.5 | 13.8 | 12.5 |
| Comp. Example CF2 | hydroxyethyl-cellulose[2] | 100 | 87.5 | 86.5 | 56.3 | 32.5 | 31.3 |
| Example F1 | Example S3 | 100 | 97.4 | 95.2 | 94.8 | 93.8 | 92.9 |

[1]Available from Ashland under the tradename PVP K-90
[2]Available from The Dow Chemical Company under tradename CELLOSIZE ™ AM-103

Durability Tests

As prepared hair curls were clamped to the holder of a shaker in a controlled humidity (50%) and temperature (25° C.) room. A given vertical shaking amplitude and frequency (50 HZ) was applied to the hair tresses using the Bodine Electric company type FPM controller. The curl length was initially and after 4 hours of shaking. The percent curl retention following 4 hours of shaking was calculated using the formula:

$$\% \text{ curl retention} = \frac{L_0 - L_t}{L_0 - L_i} \times 100\%$$

wherein $L_o$, was the length of each uncurled hair tress (i.e., 8"); $L_i$ was the initial length of each hair curl before the shaking test; and $L_t$ was the length of the hair curl after shaking for four hours. The curl retention after shaking for the treated hair curls is provided in TABLE 6.

TABLE 6

| Formulation Example | Treatment Polymer | % Curl Retention after 4 hrs |
|---|---|---|
| Comp. Example CF1 | Polyvinylpyrrolidone[1] | 60.5 |
| Comp. Example CF2 | hydroxyethylcellulose[2] | 91.7 |
| Example F1 | Example S3 | 88.6 |

[1]Available from Ashland under the tradename PVP K-90
[2]Available from The Dow Chemical Company under tradename CELLOSIZE ™ AM-103

Thickening Tests

The water thickening efficiency of the silicon modified hydroxyethyl cellulose prepared according to Example S2 was compared against several commercial benchmarks. Specifically, the Brookfield viscosity at 30 rpm of a 1.5 wt % solution of each thickener in deionized water was measured using a TA Instruments DHR-3 rheometer with an aluminum cup and bob. The results are provided in TABLE 7. Note that with the silicone modified hydroxyethyl cellulose prepared according to Example S2 delivered a viscosity of 7,500 cP, twice that of commercial Siligel. This rheological enhancement is believed to be attributed, at least in part, to silicone hydrophobe association in the water phase. While the thickening efficiency of the silicone modified hydroxyethyl cellulose prepared according to Example S2 was lower than that provided by the commercial acrylate rheology modifiers (i.e., Carbopol 980, Aculyn™ 28, Aristoflex AVC and Sepimax Zen), it is believed that further thickening can be provided by selection of a higher molecular weight hydroxyethyl cellulose backbone polymer.

TABLE 7

| Thickener | Viscosity @ 30 rpm (cP) |
|---|---|
| Example S2 | 7,500 |
| Cellosize ™ AM-103 HEC[1] | 200 |
| Xanthan gum[2] | 10,000 |
| Aculyn ™ Siltouch[3] | 30,933 |
| Carbopol 980[4] | 74,800 |
| Aculyn ™ 28[5] | 64,000 |
| Sepimax Zen[6] | 23,733 |
| Siligel[7] | 4,267 |
| Aristoflex AVC[8] | 74,800 |

[1]Available from The Dow Chemical Company
[2]Available from MakingCosmetics
[3]Available from The Dow Chemical Company
[4]Available from Lubrizol
[5]Available from The Dow Chemical Company
[6]Available from Seppic
[7]Available from Lucas Meyer Cosmetics
[8]Available from Clariant International Ltd.

Formulation Clarity

Formulation clarity is desirable for a variety of personal care compositions. A 1.5 wt % solution in deionized water of the silicon modified hydroxyethyl cellulose prepared according to Example S2 was observed to be a colorless clear solution.

Salt Tolerance

Salt resistance is desirable for a variety of personal care compositions. Rheology modifiers often lose their formulation thickening ability in the presence of salts. To assess the salt resistance of the silicon modified hydroxyethyl cellulose prepared according to Example S2 a 1.5 wt % solution in deionized water was prepared. The resulting solution was divided into three samples. To two of the samples was added sodium chloride to a concentration of 1 wt % and 5 wt %. The Brookfield viscosity of the three samples was then measured at 30 rpm using a TA Instruments DHR-3 rheometer with an aluminum cup and bob. The results are provided in TABLE 8.

TABLE 8

| wt % NaCl | Viscosity @ 30 rpm (cP) |
|---|---|
| 0 | 7,500 |
| 1.0 | 15,500 |
| 5.0 | 15,500 |

We claim:
1. A personal care composition, comprising:
    a cosmetically acceptable carrier;
    a silicon glycan of formula (I):

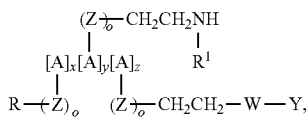

wherein each A comprises an independently selected saccharide moiety; wherein each W is an independently selected beta-amino alcohol moiety; wherein each Y comprises an independently selected organosilicon moiety; wherein each R is independently selected from the group consisting of substituted or unsubstituted hydrocarbyl groups, ether moieties, amine moieties, and H; wherein each $R^1$ is independently selected from the group consisting of substituted or unsubstituted hydrocarbyl groups and H; wherein each Z is an independently selected ether moiety; wherein each subscript o is independently 0 or 1; wherein subscripts x and y are each independently from ≥0 to <1; wherein subscript z is selected from >0 to 1; with the proviso that x+y+z=1; wherein moieties indicated by subscripts x, y, and z may be in randomized or block form in the silicon glycan; wherein (i) each saccharide moiety A is a hexose; (ii) each $R^1$ is H or a $C_{1-4}$ hydrocarbyl group; (iii) subscript o is 1 in each moiety indicated by subscript y; (iv) subscript o is 1 in each moiety indicated by subscript z; (v) in each moiety where subscript o is 1 the ether moiety Z comprises an ether of formula —$(C_tH_{2t}O)_u$—, where subscript t is independently 2 to 4 in each moiety indicated by subscript u and subscript u is 1 to 50; (v) each R is H, a $C_{1-18}$ hydrocarbyl group, a polyoxyalkylene group, or a tertiary amino group; or (vi) any combination of (i) to (v); and wherein each saccharide moiety A is a component of and collectively form a hydroxyethyl cellulose; and at least one personal care active selected from the group consisting of an absorbent; an acid; an aesthetic modifier; an antiaging agent; an antidandruff agent; an antifrizz agent; an antimicrobial agent/preservative; an antioxidant; an antiperspirant or deodorant active; an antistatic agent; a bioactive agent; a bleaching or coloration agent; a chelating agent; a cleansing surfactant; a conditioning agent; a colorant; a consistency factor; a deodorant; an emulsifying agent; an emollient; a fat; a filler; a foaming agent; a fragrance; a hair oil; a hair treatment active; a hair waving/straightening agent; a hair styling agent; a hard particle; a humectant; a lecithin; a light management powder or particle; a lubricating agent; a moisturizer; a natural ingredient; an oil; an opacifier; a pearlizing agent; a penetrant; a pH adjusting agent; a phospholipid; a pigment; a plant extract; a polymer; a preservative; a protein/amino acid; a rheology modifier; a salt; a sensory modifier; a silicone oil; a skin care active; a skin coolant; a skin protectant; a slip agent; a soap; a soft particle; a stabilizer; a sun care active; a sunscreen additive; a surfactant; a thickener; a vitamin; a water proofing agent and a wax; and
    wherein the personal care composition is a hair styling formulation.

2. The personal care composition of claim 1, wherein each beta-amino alcohol moiety W is independently selected from the group consisting of formula (i)-(iv)

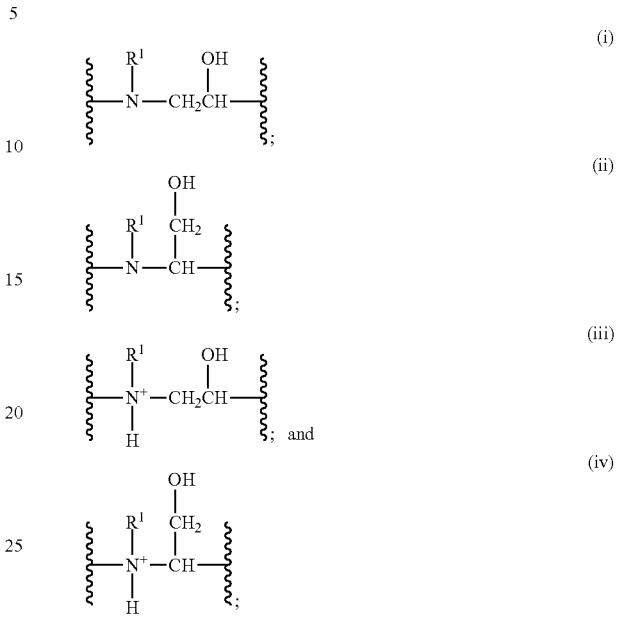

and wherein each organosilicon moiety Y is independently selected from the group consisting of a silyl moiety and an organopolysiloxane.

3. The personal care composition of claim 2, wherein the organosilicon moiety Y is the silyl moiety; and wherein the silyl moiety is of formula

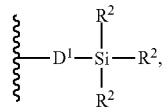

where $D^1$ is a divalent linking group; and each $R^2$ is independently selected from the group consisting of substituted or unsubstituted hydrocarbyl groups, siloxy groups, silyl groups, H, and alkylene oxide groups.

4. The personal care composition of claim 3, wherein the organosilicon moiety Y is the organopolysiloxane; and wherein the organopolysiloxane is of formula:

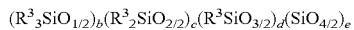

where each $R^3$ is independently selected from the group consisting of substituted or unsubstituted hydrocarbyl groups and siloxy groups, with the proviso that at least one $R^3$ is a silicon-bonded divalent linking group; and subscripts b, c, d and e are each mole fractions such that b+c+d+e=1, with the proviso that b+c+d>0.

5. The personal care composition of claim 1, wherein the personal care composition comprises the at least one personal care active of the chelating agent, emollient and preservative.

6. A method of treating hair of a mammal, comprising:
    providing the personal care composition according to claim 1; and
    applying the personal care composition to the hair of a mammal.

* * * * *